(12) United States Patent
Yoshida

(10) Patent No.: US 11,844,649 B2
(45) Date of Patent: Dec. 19, 2023

(54) ULTRASOUND PROBE AND ULTRASOUND ENDOSCOPE

(71) Applicant: OLYMPUS CORPORATION, Tokyo (JP)

(72) Inventor: Satoshi Yoshida, Kawagoe (JP)

(73) Assignee: OLYMPUS CORPORATION, Tokyo (JP)

(*) Notice: Subject to any disclaimer, the term of this patent is extended or adjusted under 35 U.S.C. 154(b) by 192 days.

(21) Appl. No.: 17/223,432

(22) Filed: Apr. 6, 2021

(65) Prior Publication Data
US 2021/0219957 A1 Jul. 22, 2021

Related U.S. Application Data

(63) Continuation of application No. PCT/JP2018/039104, filed on Oct. 19, 2018.

(51) Int. Cl.
*A61B 8/00* (2006.01)
*A61B 8/12* (2006.01)
(Continued)

(52) U.S. Cl.
CPC ............ *A61B 8/4494* (2013.01); *A61B 1/018* (2013.01); *A61B 8/12* (2013.01); *A61B 8/4444* (2013.01); *B06B 1/064* (2013.01)

(58) Field of Classification Search
CPC ........ A61B 8/12; A61B 8/4444; B06B 1/0696
See application file for complete search history.

(56) References Cited

U.S. PATENT DOCUMENTS

2005/0143657 A1* 6/2005 Roth .................. G01S 15/8934
600/459
2006/0116584 A1* 6/2006 Sudol ...................... A61B 8/12
600/459
(Continued)

FOREIGN PATENT DOCUMENTS

EP 1728563 A2 * 12/2006 ............... A61B 8/00
JP H3-275044 A 12/1991
(Continued)

OTHER PUBLICATIONS

Yuling Chen, Man Nguyen, and Jesse T. Yen, 7.5 MHz Dual-Layer Transducer Array for 3-D Rectilinear Imaging, 2011, Ultrasonic Imaging 33:3, 205-216 (Year: 2011).*

(Continued)

*Primary Examiner* — Colin T. Sakamoto
*Assistant Examiner* — Tommy T Ly
(74) *Attorney, Agent, or Firm* — Scully, Scott, Murphy & Presser, P.C.

(57) ABSTRACT

An ultrasound probe includes: an ultrasound transducer including plural piezoelectric elements; an acoustic lens layer configured to radiate the ultrasound emitted from the plural piezoelectric elements to outside; a back layer that faces the acoustic lens layer with the ultrasound transducer interposed between the back layer and the acoustic lens layer; and a wiring member having at least a part that is arranged at a first position between the acoustic lens layer and the ultrasound transducer or at a second position that faces the ultrasound transducer with the back layer interposed between the second position and the ultrasound transducer. The wiring member includes: a resin layer having electrically insulating; and an electrically conducting layer that is provided on the resin layer and includes plural signal wirings.

15 Claims, 11 Drawing Sheets

(51) Int. Cl.
*B06B 1/06* (2006.01)
*A61B 1/018* (2006.01)

(56) References Cited

U.S. PATENT DOCUMENTS

| | | | |
|---|---|---|---|
| 2007/0157732 A1* | 7/2007 | Lee | B06B 1/0629 73/634 |
| 2008/0125658 A1* | 5/2008 | Lee | B06B 1/0622 600/459 |
| 2009/0306518 A1* | 12/2009 | Kurse | B06B 1/0629 600/466 |
| 2010/0204583 A1* | 8/2010 | Rhim | A61B 8/00 600/459 |
| 2013/0018269 A1* | 1/2013 | Matsumoto | A61B 8/4494 600/459 |
| 2013/0188446 A1* | 7/2013 | Kubota | B06B 1/0622 367/7 |
| 2016/0143618 A1* | 5/2016 | Park | A61B 8/4477 600/459 |
| 2019/0090857 A1* | 3/2019 | Yamamoto | A61B 8/4488 |
| 2019/0350554 A1* | 11/2019 | Wildes | H01L 41/0472 |
| 2020/0255653 A1* | 8/2020 | Nakai | C08G 59/06 |

FOREIGN PATENT DOCUMENTS

| | | |
|---|---|---|
| JP | H8-122311 A | 5/1996 |
| JP | 2002-224104 A | 8/2002 |
| JP | 2004-298240 A | 10/2004 |
| JP | 2010-154382 A | 7/2010 |
| JP | 2010154382 A * | 7/2010 |
| JP | 2012-249777 A | 12/2012 |
| JP | 2013-150681 A | 8/2013 |
| WO | 2011/033666 A1 | 3/2011 |

OTHER PUBLICATIONS

K. Kirk Shung, Diagnostic Ultrasound: Imaging and Blood Flow Measurements, 2015, CRC Press, Second Edition, p. 58 (Year: 2015) (Year: 2015).*
International Search Report dated Jan. 15, 2019 issued in PCT/JP2018/039104.
Japanese Office Action dated Mar. 8, 2022 received in 2020-551715.

* cited by examiner

ULTRASOUND PROBE AND ULTRASOUND ENDOSCOPE

CROSS-REFERENCE TO RELATED APPLICATION

This application is a continuation of International Application No. PCT/JP2018/039104, filed on Oct. 19, 2018, the entire contents of which are incorporated herein by reference.

BACKGROUND

1. Technical Field

The present disclosure relates to ultrasound probes and ultrasound endoscopes.

2. Related Art

In the related art, ultrasound probes each including plural piezoelectric elements have been known (see, for example, Japanese Patent Application Laid-open No. 2002-224104). Each of the plural piezoelectric elements emits ultrasound according to an electric signal input.

An ultrasound probe or an ultrasound array transducer described in Japanese Patent Application Laid-open No. 2002-224104 is a convex ultrasound probe. More specifically, in addition to plural piezoelectric elements, the ultrasound probe includes an acoustic matching layer, an acoustic lens layer, a backing material, and a cable wiring substrate.

A ground electrode is provided on a front outer surface of outer surfaces of each piezoelectric element. Furthermore, a signal electrode is provided on a back outer surface of the outer surfaces of the piezoelectric element, the back outer surface facing inside and being on the back of the front outer surface.

The cable wiring substrate is provided in contact with and vertically to each of the signal electrodes provided on the plural piezoelectric elements. An electric signal is input to each of the signal electrodes via the cable wiring substrate. Each of the plural piezoelectric elements emits ultrasound according to the electric signal input.

SUMMARY

In some embodiments, an ultrasound probe includes: an ultrasound transducer including plural piezoelectric elements that are arranged in parallel along a first direction, each piezoelectric element being configured to emit ultrasound according to an electric signal input; an acoustic lens layer configured to radiate the ultrasound emitted from the plural piezoelectric elements to outside; a back layer that faces the acoustic lens layer with the ultrasound transducer interposed between the back layer and the acoustic lens layer, and has electric conductivity; and a wiring member having at least a part that is arranged at a first position between the acoustic lens layer and the ultrasound transducer or at a second position that faces the ultrasound transducer with the back layer interposed between the second position and the ultrasound transducer. The wiring member includes: a resin layer having electrically insulating; and an electrically conducting layer that is provided on the resin layer and includes plural signal wirings through which the electric signals that respectively cause the plural piezoelectric elements to emit the ultrasound are supplied to the plural piezoelectric elements, the plural signal wirings being respectively connected electrically to the plural piezoelectric elements.

In some embodiments, an ultrasound endoscope includes an insertion portion to be inserted into a subject. The insertion portion includes, at a distal end of the insertion portion: an ultrasound transducer including plural piezoelectric elements that are arranged in parallel along a first direction, each piezoelectric element being configured to emit ultrasound according to an electric signal input; an acoustic lens layer configured to radiate the ultrasound emitted from the plural piezoelectric elements to outside; a back layer that faces the acoustic lens layer with the ultrasound transducer interposed between the back layer and the acoustic lens layer, and has electric conductivity; and a wiring member having at least a part that is arranged at a first position between the acoustic lens layer and the ultrasound transducer or at a second position that faces the ultrasound transducer with the back layer interposed between the second position and the ultrasound transducer. The wiring member includes: a resin layer having electrically insulating; and an electrically conducting layer that is provided on the resin layer and includes plural signal wirings through which the electric signals that respectively cause the plural piezoelectric elements to emit the ultrasound are supplied to the plural piezoelectric elements, the plural signal wirings being respectively connected electrically to the plural piezoelectric elements.

The above and other features, advantages and technical and industrial significance of this disclosure will be better understood by reading the following detailed description of presently preferred embodiments of the disclosure, when considered in connection with the accompanying drawings.

DETAILED DESCRIPTION

Modes, hereinafter referred to as embodiments, for carrying out the disclosure will be described below by reference to the drawings. The disclosure is not limited by the embodiments described below. Furthermore, any portions that are the same will be assigned with the same reference sign, throughout the drawings.

First Embodiment

Schematic Configuration of Endoscope System

Figure 1:
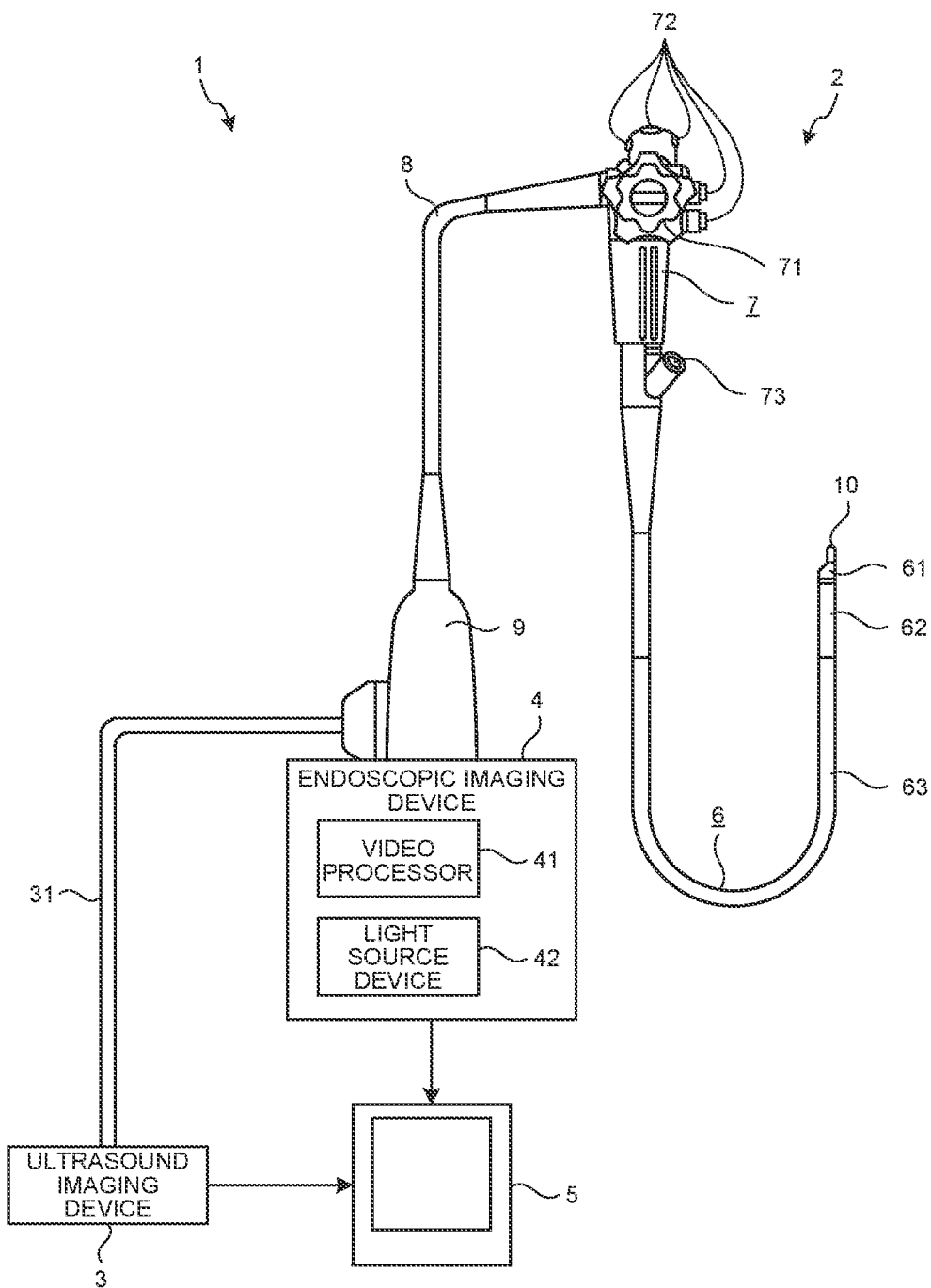
FIG. 1 is a diagram illustrating an endoscope system according to a first embodiment.

FIG. 1 is a diagram illustrating an endoscope system 1 according to a first embodiment.

The endoscope system 1 is a system for ultrasound diagnosis and treatment of the interior of a subject, such as a human, using an ultrasound endoscope. This endoscope system 1 includes, as illustrated in FIG. 1, an ultrasound endoscope 2, an ultrasound imaging device 3, an endoscopic imaging device 4, and a display device 5.

A part of the ultrasound endoscope 2 is capable of being inserted into a subject, and the ultrasound endoscope 2 includes: a function of outputting an echo signal by transmitting ultrasound pulses or acoustic pulses toward body walls in the subject and receiving ultrasound echoes reflected by the subject; and a function of outputting an image signal by imaging the interior of the subject.

A detailed configuration of the ultrasound endoscope 2 will be described later.

The ultrasound imaging device 3 is electrically connected to the ultrasound endoscope 2 via an ultrasound cable 31 (FIG. 1), and outputs a pulse signal to the ultrasound endoscope 2 and inputs an echo signal from the ultrasound endoscope 2, both via the ultrasound cable 31. An ultrasound image is generated in the ultrasound imaging device 3 by predetermined processing of the echo signal.

A later described endoscope connector 9 (FIG. 1) of the ultrasound endoscope 2 is detachably connected to the endoscopic imaging device 4. The endoscopic imaging device 4 includes, as illustrated in FIG. 1, a video processor 41 and a light source device 42.

The video processor 41 inputs an image signal from the ultrasound endoscope 2 via the endoscope connector 9. The video processor 41 then generates an endoscopic image by performing predetermined processing of the image signal.

The light source device 42 supplies illumination light for illuminating the interior of a subject, to the ultrasound endoscope 2 via the endoscope connector 9.

The display device 5 is formed using liquid crystal, organic electroluminescence (EL), a cathode ray tube (CRT), or a projector, and displays, for example, an ultrasound image generated by the ultrasound imaging device 3 or an endoscopic image generated by the endoscopic imaging device 4.

Configuration of Ultrasound Endoscope

A configuration of the ultrasound endoscope 2 will be described next.

The ultrasound endoscope 2 includes, as illustrated in FIG. 1, an insertion portion 6, an operating unit 7, a universal cord 8, and the endoscope connector 9.

Figure 2:
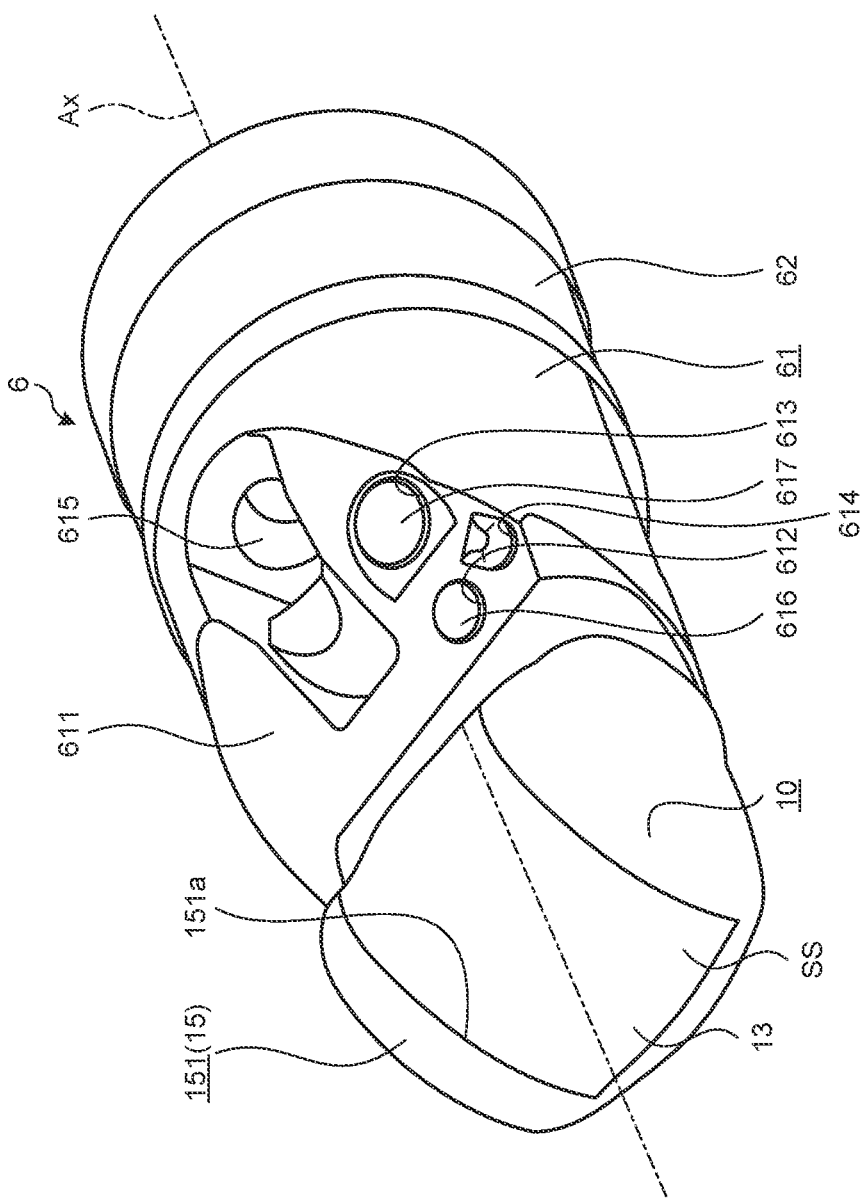
FIG. 2 is a perspective view illustrating a distal end of an insertion portion.

FIG. 2 is a perspective view illustrating a distal end of the insertion portion 6.

In describing a configuration of the insertion portion 6 below, the distal end of the insertion portion 6 (the distal end to be inserted into a subject) will simply be referred to as "the distal end" and a proximal end of the insertion portion 6 (the other end away from the distal end of the insertion portion 6) will simply be referred to as "the proximal end".

The insertion portion 6 is a portion to be inserted into a subject. This insertion portion 6 includes, as illustrated in FIG. 1 or FIG. 2, an ultrasound probe 10 provided at the distal end; a rigid member 61 connected to a proximal end of the ultrasound probe 10; a bending portion 62 that is connected to a proximal end of the rigid member 61 and is bendable; and a flexible tube 63 (FIG. 1) that is connected to a proximal end of the bending portion 62 and has flexibility.

The insertion portion 6, the operating unit 7, the universal cord 8, and the endoscope connector 9 include: laid therethrough, a light guide (not illustrated in the drawings) that transmits illumination light supplied from the light source device 42, a transducer cable CB (see FIG. 3) that transmits the above described pulse signal and echo signal, and a signal cable (not illustrated in the drawings) that transmits an image signal; and provided therethrough, a pipe line (not illustrated in the drawings) for circulating fluid.

The rigid member 61 is a rigid member formed of a resin material, for example, and has an approximately cylindrical shape extending along an insertion axis Ax (FIG. 2). The insertion axis Ax is an axis along which the insertion portion 6 extends.

This rigid member 61 has a sloped surface 611 formed on the rigid member 61's outer peripheral surface at the rigid member 61's distal end, the sloped surface 611 making the rigid member 61 tapered toward the distal end of the rigid member 61.

The rigid member 61 also includes, as illustrated in FIG. 2, formed therein, for example: an attachment hole (not illustrated in the drawings) penetrating the rigid member 61 from its proximal end to its distal end; and an illumination hole 612, an imaging hole 613, a gas and water feeding hole 614, and an instrument channel 615 that each penetrate through the rigid member 61 from its proximal end to the sloped surface 611.

The attachment hole (not illustrated in the drawings) is a hole where the ultrasound probe 10 is attached. The attachment hole includes therein the transducer cable CB (see FIG. 3) inserted therethrough.

An emitting end of the above mentioned light guide (not illustrated in the drawings) and an illumination lens 616 (FIG. 2) through which illumination light emitted from the emitting end of the light guide is emitted into a subject are arranged in the illumination hole 612.

An objective optical system 617 (FIG. 2) that condenses light (a subject image) that has been emitted into the subject and reflected inside the subject, and an imaging element (not illustrated in the drawings) that captures the subject image condensed by the objective optical system 617 are arranged in the imaging hole 613. An image signal captured by the imaging element is transmitted to the endoscopic imaging device 4 (the video processor 41) via the above mentioned signal cable (not illustrated in the drawings).

As described above, according to this first embodiment, the illumination hole 612 and the imaging hole 613 are formed on the sloped surface 611. Therefore, the ultrasound endoscope 2 according to the first embodiment is formed as an oblique viewing endoscope for observation in a direction intersecting the insertion axis Ax at an acute angle.

The gas and water feeding hole 614 forms a part of the above mentioned pipe line (not illustrated in the drawings) and is a hole for feeding gas or water toward the imaging hole 613 to wash an outer surface of the objective optical system 617.

The instrument channel 615 is a channel through which a treatment tool (not illustrated in the drawings), such as a puncture needle, that has been inserted through the insertion portion 6 is caused to protrude outside.

The operating unit 7 is a portion that is connected to the proximal end of the insertion portion 6 and receives various operations from a medical doctor, for example. This operating unit 7 includes, as illustrated in FIG. 1, a bending knob 71 for operating the bending portion 62 to bend, and plural operating members 72 for performing various operations.

Furthermore, the operating unit 7 includes, provided therein, a treatment tool insertion opening 73 (FIG. 1) that communicates with the instrument channel 615 via a tube (not illustrated in the drawings) provided inside the bending portion 62 and flexible tube 63, the treatment tool insertion opening 73 being for inserting a treatment tool (not illustrated in the drawings) through the tube.

The universal cord 8 is a cord that extends from the operating unit 7 and includes, arranged therein: the above mentioned light guide (not illustrated in the drawings), transducer cable CB, and signal cable (not illustrated in the drawings); as well as a tube (not illustrated in the drawings) that is a part of the above mentioned pipe line (not illustrated in the drawings).

The endoscope connector 9 is provided at an end portion of the universal cord 8. The ultrasound cable 31 is connected to the endoscope connector 9 that is connected to the video processor 41 and light source device 42 by being plugged into the endoscopic imaging device 4.

Configuration of Ultrasound Probe

A configuration of the ultrasound probe 10 will be described next.

Figure 3:
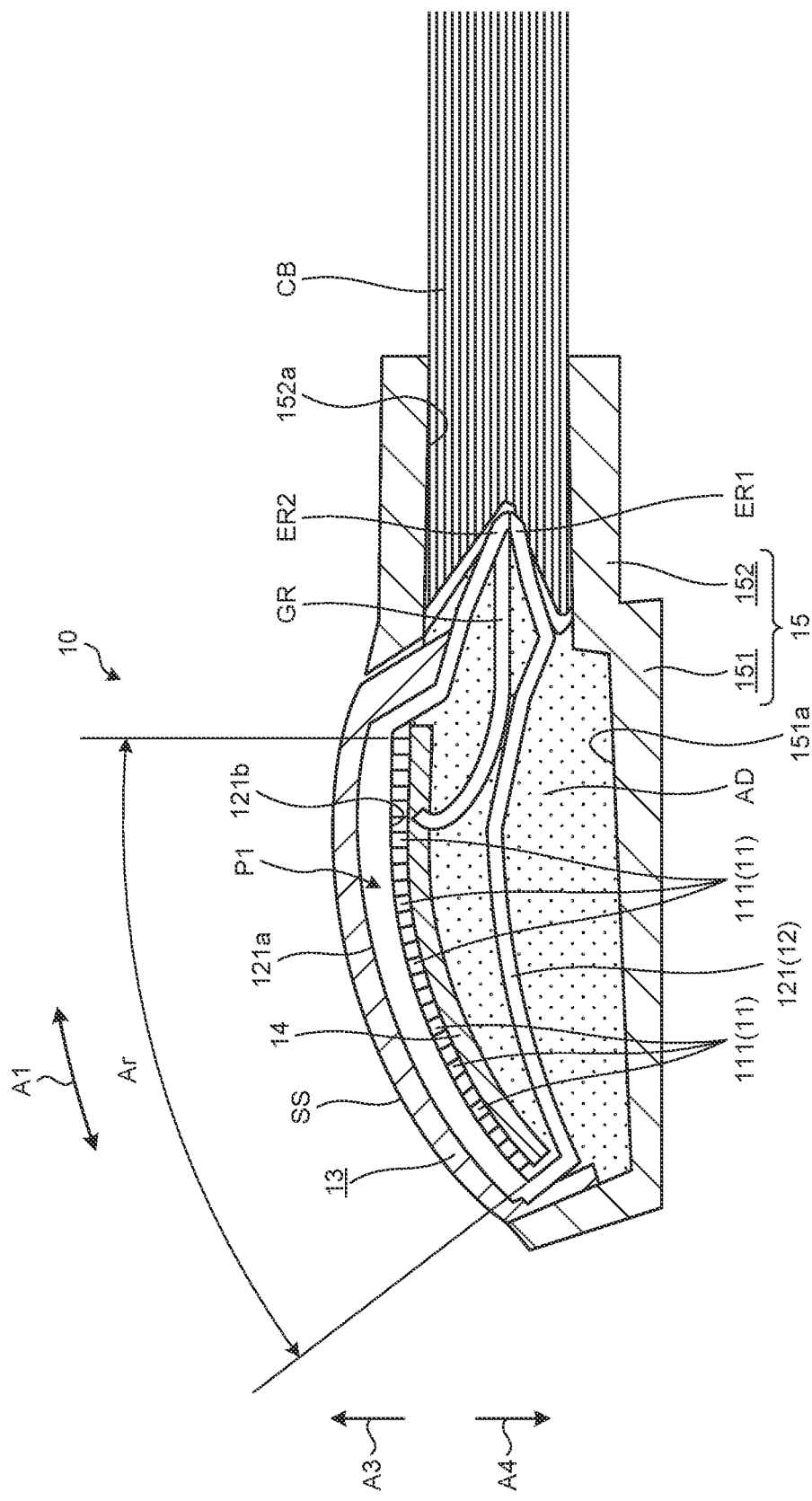
FIG. 3 is a sectional view illustrating an ultrasound probe.

FIG. 3 is a sectional view illustrating the ultrasound probe 10. Specifically, FIG. 3 is a sectional view of the ultrasound probe 10, the sectional view being taken upon a plane that includes the insertion axis Ax and is orthogonal to a scanning surface SS.

The ultrasound probe 10 is a convex ultrasound probe and has the scanning surface SS that is convex outward (upward in FIG. 3) and is a cylindrical surface. The scanning surface SS is a part of an outer front surface of the ultrasound probe 10.

Figure 4:
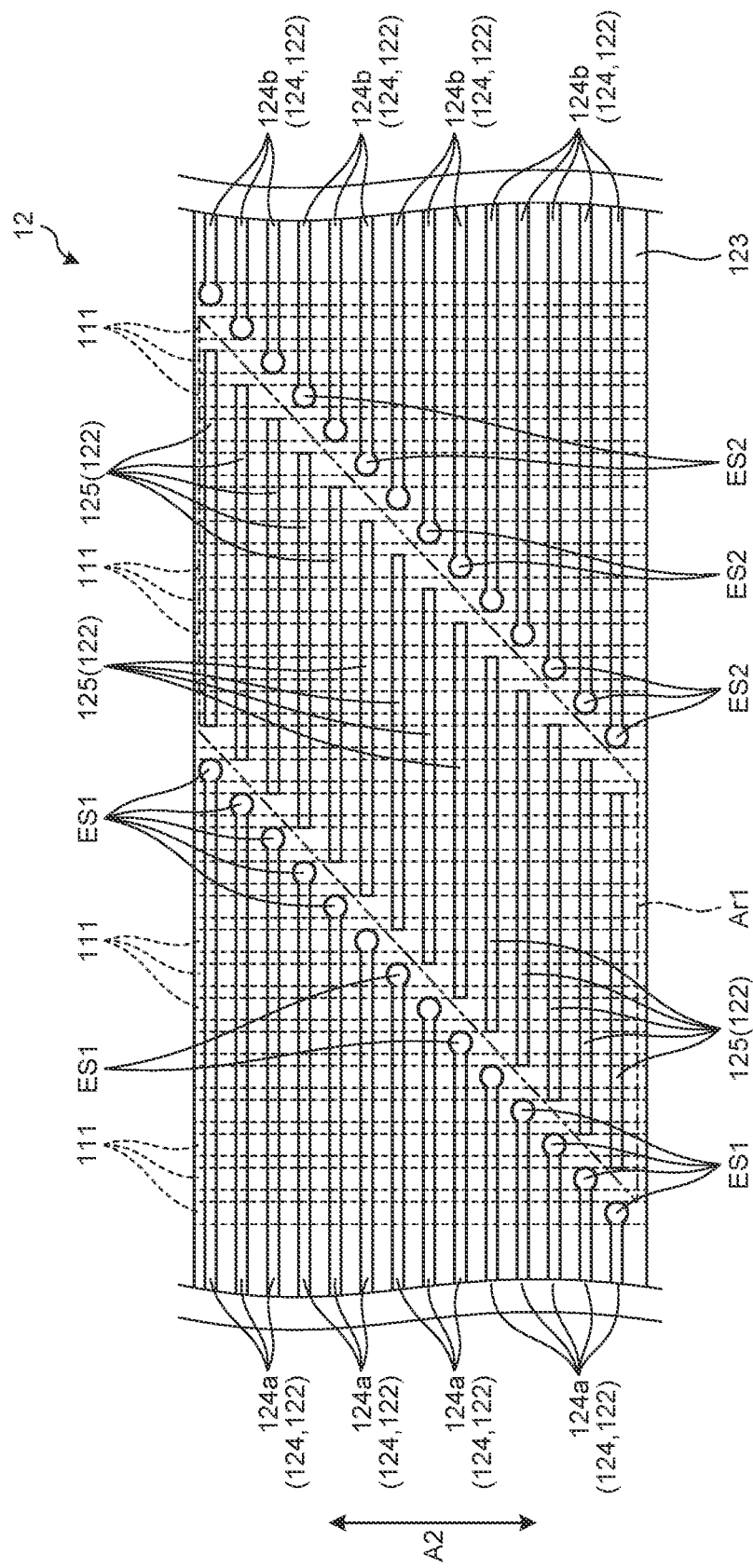
FIG. 4 is a diagram illustrating a structure of connection between an ultrasound transducer and a wiring member.

In describing the configuration of the ultrasound probe 10 below, the circumferential direction of the cylindrical scanning surface SS will be referred to as a first direction A1 (FIG. 3) and the direction along the cylindrical axis of the cylindrical scanning surface SS (the direction orthogonal to the plane of paper in FIG. 3) will be referred to as a second direction A2 (FIG. 4). Furthermore, upward in FIG. 3 will be referred to as the outer front A3 (FIG. 3), and downward in FIG. 3 will be referred to as the back A4 (FIG. 3).

The ultrasound probe 10 scans, or transmits and receives, ultrasound along the first direction A1 in an ultrasound transmission and reception area Ar (FIG. 3) that is formed of normal lines of the scanning surface SS, the ultrasound transmission and reception area Ar having a fan shape in the sectional view.

This ultrasound probe 10 includes, as illustrated in FIG. 3, an ultrasound transducer 11, a wiring member 12, an acoustic lens layer 13, a back layer 14, and a holding member 15.

The ultrasound transducer 11 includes, as illustrated in FIG. 3, plural piezoelectric elements 111.

The plural piezoelectric elements 111 are each formed of an elongated rectangular parallelepiped linearly extending along the second direction A2, and are regularly arrayed along the first direction A1 as illustrated in FIG. 3. Furthermore, first and second electrodes 111a and 111b (see FIG. 5 and FIG. 6) are formed on outer surfaces of the piezoelectric elements 111. The piezoelectric elements 111 convert a pulse signal input via the transducer cable CB, wiring member 12, back layer 14, and first and second electrodes 111a and 111b into ultrasound pulses and transmit the ultrasound pulses toward a subject, the pulse signal corresponding to an electric signal according to the disclosure. The piezoelectric elements 111 also convert ultrasound echoes reflected by the subject into an electric echo signal and output the electric echo signal to the transducer cable CB via the first and second electrodes 111a and 111b, back layer 14, and wiring member 12.

The piezoelectric elements 111 are formed using PMN-PT single crystal, PMN-PZT single crystal, PZN-PT single crystal, PIN-PZN-PT single crystal, or a relaxor-based material.

PMN-PT single crystal is an abbreviation of a solid solution of lead magnesium niobate and lead titanate. PMN-PZT single crystal is an abbreviation of a solid solution of lead magnesium niobate and lead zirconate titanate.

PZN-PT single crystal is an abbreviation of a solid solution of lead zinc niobate and lead titanate. PIN-PZN-PT single crystal is an abbreviation of a solid solution of lead indium niobate, lead zinc niobate, and lead titanate. The relaxor-based material is a general term for ternary system piezoelectric materials including lead zirconate titanate (PZT) and lead-based complex perovskite that is added as a relaxor material to increase the piezoelectric constant and dielectric constant. Lead-based complex perovskite is represented by $Pb(B1,B2)O_3$ where B1 is magnesium, zinc, indium, or scandium, and B2 is niobium, tantalum, or tungsten. These materials have excellent piezoelectric effect. Therefore, even if downsizing is implemented, the value of electric impedance is able to be reduced, and this is favorable in terms of impedance matching between the first and second electrodes 111a and 111b.

The first and second electrodes 111a and 111b are each formed of a metallic material or a resin material having electric conductivity, and are formed on the following respective outer surfaces of the piezoelectric elements 111.

The first electrodes 111a are each formed all over an outer surface of the piezoelectric element 111, the outer surface being at the outer front A3. The first electrodes 111a are electrically connected to plural signal wirings 124 (see FIG. 4 and FIG. 5) provided in the wiring member 12 and function as signal electrodes that input and output signals to the piezoelectric elements 111.

The second electrodes 111b are each formed all over an outer surface of the piezoelectric element 111, the outer surface being at the back A4. That is, the first electrodes 111a and the second electrodes 111b face each other along the normal lines of the scanning surface SS with the piezoelectric elements 111 interposed between the first electrodes 111a and the second electrodes 111b. The second electrodes 111b are electrically connected to a ground line GR (FIG. 3) of the transducer cable CB and function as ground electrodes.

Figure 5:
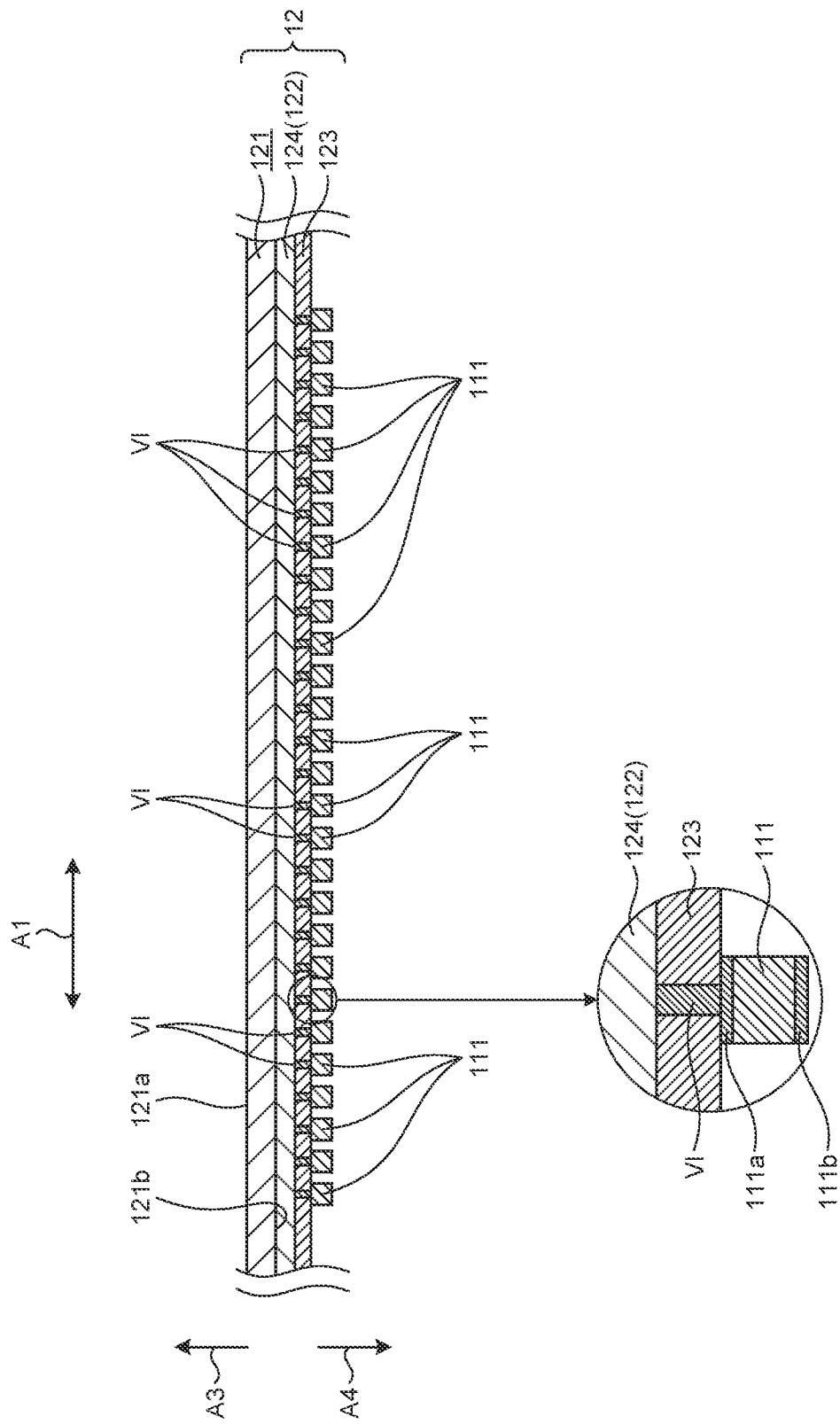
FIG. 5 is a diagram illustrating the structure of the connection between the ultrasound transducer and the wiring member.

FIG. 4 and FIG. 5 are diagrams illustrating a structure of connection between the ultrasound transducer 11 and the wiring member 12. Specifically, FIG. 4 is a plan view of a part of the wiring member 12, the part being provided at a first position P1 (FIG. 3) between the ultrasound transducer 11 and the acoustic lens layer 13 and being viewed from the outer front A3. In FIG. 4, for convenience of explanation, illustration of a resin layer 121 has been omitted. FIG. 5 is an enlarged sectional view of a part of FIG. 3. In FIG. 5, for convenience of explanation, the plural signal wirings 124 have been illustrated as a single member serving as an electrically conducting layer 122.

The wiring member 12 is a member that electrically connects signal lines (not illustrated in the drawings) of the transducer cable CB and the first electrodes 111a provided on the plural piezoelectric elements 111 respectively to each other. The wiring member 12 in this first embodiment is formed of a flexible printed circuit (FPC). The wiring member 12 includes, as illustrated in FIG. 3 to FIG. 5, the resin layer 121 (FIG. 3 and FIG. 5), the electrically conducting layer 122, and an insulating layer 123. In FIG. 3, for the convenience of explanation, illustration of the electrically conducting layer 122 and insulating layer 123 has been omitted.

The resin layer 121 is an elongated sheet (a substrate) formed of an insulating material, such as a polyimide, and having flexibility. The pair of the front and back surfaces of the sheet will be hereinafter be referred to as a first surface 121a and a second surface 121b (FIG. 3 and FIG. 5). This resin layer 121 is, as illustrated in FIG. 3, folded back such that the first surface 121a forms an outer front surface of the resin layer 121. In other words, the resin layer 121 is folded back such that the second surface 121b is positioned inside. The ultrasound transducer 11 and back layer 14 are arranged inside the resin layer 121 that has been folded back. That is, a part of the wiring member 12 is arranged at the first position P1 (FIG. 3) between the ultrasound transducer 11 and the acoustic lens layer 13.

The electrically conducting layer 122 includes, as illustrated in FIG. 4, the plural signal wirings 124 and plural dummy wirings 125.

The plural signal wirings 124 are signal wirings that are formed of a metallic material or a resin material having electric conductivity and transmit the above mentioned pulse signal and echo signal between the signal wirings (not illustrated in the drawings) of the transducer cable CB and the respective first electrodes 111a provided on the plural piezoelectric elements 111. These plural signal wirings 124 include, as illustrated in FIG. 4, plural (14 in the example of FIG. 4) first signal wirings 124a and plural (14 in the example of FIG. 4) second signal wirings 124b.

The plural first signal wirings 124a are formed respectively as wiring patterns each extending on the second surface 121b from one end ER1 (FIG. 3) to the other end ER2 (FIG. 3) of the resin layer 121, the one end ER1 and the other end ER2 being at ends of a longitudinal length of the resin layer 121, the wiring patterns being arranged in parallel along a width direction (the second direction A2) of the resin layer 121. These plural first signal wirings 124a have lengths different from one another, as illustrated in FIG. 4, the lengths being along the longitudinal direction of the resin layer 121. In the example of FIG. 4, the first signal wiring 124a that is positioned uppermost in FIG. 4 has the longest length, and the lower the plural first signal wirings 124a are arranged in FIG. 4, the shorter their lengths are.

The plural second signal wirings 124b are formed of a metallic material or a resin material having electric conductivity, each extend from the other end ER2 to the one end ER1 of the resin layer 121, the other end ER2 and the one end ER1 being at the ends of the longitudinal length of the resin layer 121, and are formed as wiring patterns arranged in parallel along the width direction (the second direction A2) of the resin layer 121. These plural second signal wirings 124b have lengths different from one another, as illustrated in FIG. 4, the lengths being along the longitudinal direction of the resin layer 121. In the example of FIG. 4, the second signal wiring 124b that is positioned lowermost in FIG. 4 has the longest length, and the upper the plural second signal wirings 124b are arranged in FIG. 4, the shorter their lengths are.

A parallelogram area Ar1 is formed on the second surface 121b, between: end portions ES1 (FIG. 4) of the plural first signal wirings 124a, the end portions ES1 being toward the other end ER2; and end portions ES2 (FIG. 4) of the plural second signal wirings 124b, the end portions ES2 being toward the one end ER1.

The plural dummy wirings 125 are dummy wiring patterns that are formed of a metallic material or a resin material having electric conductivity and are each formed in the area Ar1 on the second surface 121b. The dummy wiring patterns are wiring patterns that are not electrically connected to any member. In this first embodiment, the number of the dummy wirings 125 provided is the same as the number of the first or second signal wirings 124a or 124b, and are respectively provided on lines joining between the end portions ES1 and the end portions ES2 that face each other.

The plural signal wirings 124 and the dummy wirings 125 in this first embodiment are formed of the same material and have the same width dimension and thickness dimension.

The insulating layer 123 is formed of an insulating material, such as polyimide. This insulating layer 123 is provided at a position that faces the resin layer 121 (the second surface 121b) with the electrically conducting layer 122 interposed between the insulating layer 123 and the resin layer 121, provides insulation of the electrically conducting layer 122, and protects the electrically conducting layer 122. This insulating layer 123 includes, as illustrated in FIG. 5, vias VI respectively provided at positions that face the end portions ES1 and ES2. The vias VI are respectively connected electrically to the end portions ES1 and ES2 and are respectively connected electrically to the first electrodes 111a provided on the plural piezoelectric elements 111. That is, the plural signal wirings 124 are respectively connected electrically to the first electrodes 111a (plural piezoelectric elements 111) via the vias VI.

Although specific illustration has been omitted in the drawings, vias are respectively provided in the insulating layer 123, at positions that face the end portions of the plural first signal wirings 124a being toward the one end ER1 and the end portions of the plural second signal wirings 124b being toward the other end ER2. The vias are respectively connected electrically to these end portions and are also respectively connected electrically to the signal lines of the transducer cable CB. Positions at which the wiring member 12 and the signal wirings of the transducer cable CB are connected to each other are, as illustrated in FIG. 3, positioned more toward the proximal end than the ultrasound transducer 11, acoustic lens layer 13, and the back layer 14 are.

In a case where a part of the wiring member 12 is arranged at the first position P1, the wiring member 12 is preferably caused to function as an acoustic matching layer that causes the acoustic impedance of the ultrasound transducer 11 and the acoustic impedance of a subject to match each other, in order to transmit sound (ultrasound) efficiently between the ultrasound transducer 11 and the subject.

Specifically, the wiring member 12 preferably has an acoustic impedance that is between that of the ultrasound transducer 11 and that of the acoustic lens layer 13. For example, acoustic impedances of the resin layer 121 and the insulating layer 123 are preferably 2 MRayl to 20 MRayl. Furthermore, the acoustic impedances of the resin layer 121 and the insulating layer 123 preferably decrease in order from the ultrasound transducer 11 toward the acoustic lens layer 13. For example, the insulating layer 123 may have an acoustic impedance of 9 MRayl and the resin layer 121 may have an acoustic impedance of 2 MRayl. Furthermore, thicknesses of the resin layer 121 and insulating layer 123 are preferably equal to or less than ¼ of a wavelength λ (for example, 400 μm to 500 μm) at the center frequency of ultrasound transmitted from the ultrasound transducer 11 and transmitted through the resin layer 121 and insulating layer 123. In addition, the electrically conducting layer 122 preferably has a thickness equal to or less than ¹⁄₂₅ of that wavelength λ.

The acoustic lens layer 13 is, as illustrated in FIG. 3, fixed on the first surface 121a of the resin layer 121, at the part of the wiring member 12 arranged at the first position P1, by adhesive force due to an adhesive (not illustrated in the drawings) or sticking force in cast molding of the lens material itself. That is, a surface of the acoustic lens layer 13 serves as the scanning surface SS, the surface being at the outer front A3. This scanning surface SS has an arc shape extending along the first direction A1 in its sectional view and also has an arc shape extending along the second direction A2 in its sectional view. That is, the scanning surface SS has a convex shape protruding to the outer front A3. The acoustic lens layer 13 converges ultrasound pulses transmitted from the ultrasound transducer 11 and transmitted through the part of the wiring member 12, the part being arranged at the first position P1. Furthermore, the acoustic lens layer 13 transmits ultrasound echoes reflected by a subject to the part of the wiring member 12, the part being arranged at the first position P1.

Figure 6:
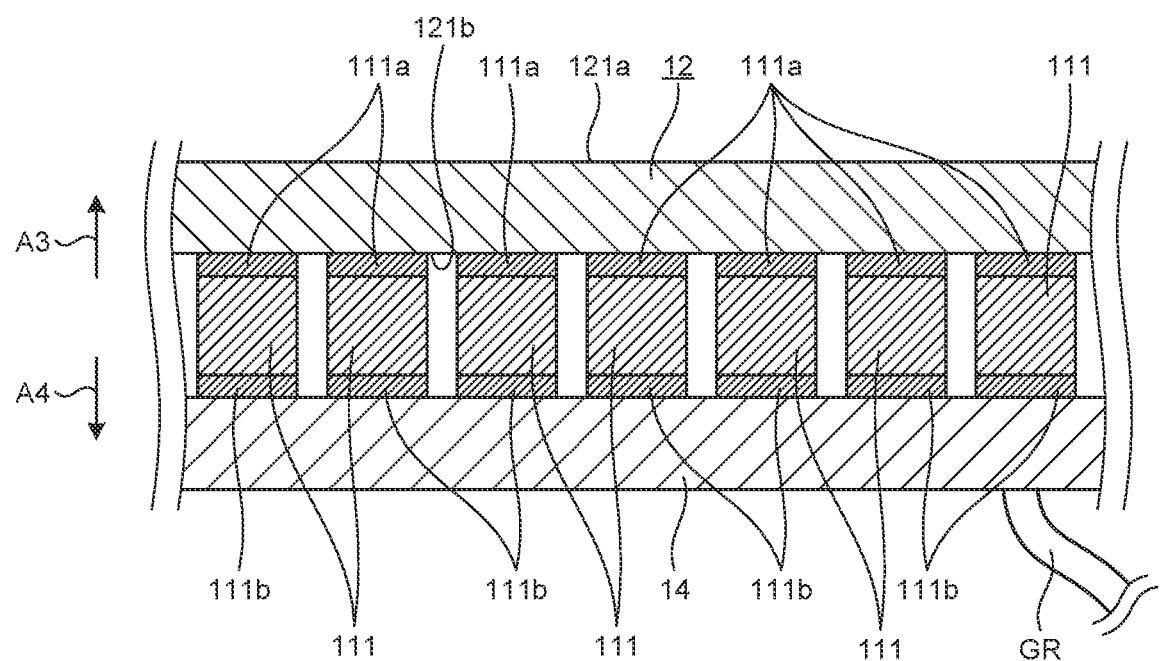
FIG. 6 is a diagram illustrating a back layer.

FIG. 6 is a diagram illustrating the back layer 14. Specifically, FIG. 6 is an enlarged sectional view of a part of FIG. 3.

The back layer 14 is provided at the back A4 of the ultrasound transducer 11, to face the acoustic lens layer 13 with the ultrasound transducer 11 interposed between the back layer 14 and the acoustic lens layer 13. In this first embodiment, the back layer 14 has an acoustic impedance larger than that of the ultrasound transducer 11 and functions as a dematching layer having electric conductivity and formed of tungsten, for example. That is, the back layer 14 has a function of increasing ultrasound incident on a subject by bouncing back, toward the subject, ultrasound transmitted from the ultrasound transducer 11 and heading in the direction opposite to the subject, that is, to the back A4. The back layer 14 is electrically connected to each of the second electrodes 111b provided on the plural piezoelectric elements 111. Furthermore, as illustrated in FIG. 3 or FIG. 6, the ground line GR of the transducer cable CB is electrically connected to the back layer 14. That is, the second electrodes 111b provided on the plural piezoelectric elements 111 are electrically connected to the ground line GR via the back layer 14.

The holding member 15 includes, as illustrated in FIG. 3, a holding portion 151 and an attachment portion 152.

The holding portion 151 is a portion that holds a unit of the ultrasound transducer 11, the wiring member 12, the acoustic lens layer 13, and the back layer 14 all unified together. This holding portion 151 includes, formed therein, as illustrated in FIG. 3, a concave portion 151a that holds the unit and causes the scanning surface SS of the acoustic lens layer 13 to be exposed outside. An adhesive AD (FIG. 3) fills in the interspace between the concave portion 151a and the unit.

The attachment portion 152 is a portion that is unitarily formed with a proximal end of the holding portion 151, inserted into the above mentioned attachment hole (not illustrated in the drawings) in the rigid member 61, and attached to the rigid member 61. This attachment portion 152 includes, as illustrated in FIG. 3, an insertion hole 152a which penetrates through the attachment portion 152 from a proximal end of the attachment portion 152 to the concave portion 151a and through which the transducer cable CB is inserted.

The above described first embodiment has the following effects.

The ultrasound probe 10 according to the first embodiment includes the wiring member 12 having a part that is arranged at the first position P1. The wiring member 12 electrically connects the signal lines (not illustrated in the drawings) of the transducer cable CB and the first electrodes 111a provided on the plural piezoelectric elements 111 respectively to each other.

Therefore, a wiring substrate does not need to be arranged at the back A4 of the plural piezoelectric elements 111 as conventionally done. In other words, a large space is not needed at the back A4 of the plural piezoelectric elements 111. That is, the ultrasound probe 10 is able to be downsized.

Furthermore, the wiring member 12 functions as an acoustic matching layer. In addition, the back layer 14 is formed of a dematching layer electrically connected to each of the second electrodes 111b provided on the plural piezoelectric elements 111, the dematching layer having electrical conductivity, and the ground line GR is electrically connected to the back layer 14.

Therefore, even if a part of the wiring member 12 is arranged at the first position P1, ultrasound is able to be efficiently transmitted between the ultrasound transducer 11 and a subject and the acoustic performance is not degraded.

Therefore, the ultrasound probe 10 according to the first embodiment is able to be downsized without being degraded in acoustic performance.

Furthermore, in the ultrasound probe 10 according to the first embodiment, the plural first signal wirings 124a extend from the one end ER1 toward the other end ER2 and have lengths along the longitudinal direction of the resin layer 121, the lengths being different from one another. In addition, the plural second signal wirings 124b each extend from the other end ER2 toward the one end ER1 and have lengths along the longitudinal direction of the resin layer 121, the lengths being different from one another.

Therefore, even if the wiring space for the plural signal wirings 124 on the second surface 121b is narrow, the plural signal wirings 124 are able to be wired efficiently, and the signal lines (not illustrated in the drawings) of the transducer cable CB and the first electrodes 111a are able to be connected electrically by the plural signal wirings 124 respectively to each other.

Furthermore, the wiring member 12 in the ultrasound probe 10 according to the first embodiment has a configuration including the electrically conducting layer 122 sandwiched between the resin layer 121 and the insulating layer 123. The plural signal wirings 124 are respectively connected electrically to the first electrodes 111a respectively via the plural vias VI provided in the insulating layer 123.

Therefore, insulation of the electrically conducting layer 122 is able to be provided sufficiently, and the signal lines (not illustrated in the drawings) of the transducer cable CB and the first electrodes 111a are able to be connected electrically to each other respectively by the wiring member 12.

The electrically conducting layer 122 in the ultrasound probe 10 according to the first embodiment includes the dummy wirings 125 formed of a material that is the same as that of the signal wirings 124 and having a width dimension and a thickness dimension that are the same as those of the signal wirings 124.

Therefore, no matter which position the ultrasound transmitted by the ultrasound transducer 11 is transmitted from, the ultrasound is transmitted through a same volume of the electrically conducting layer 122. Therefore, variation in the acoustic performance is able to be reduced.

Second Embodiment

A second embodiment will be described next.

In the following description, any component that is the same as that of the above described first embodiment will be assigned with the same reference sign, and detailed description thereof will be omitted or simplified.

Figure 7:
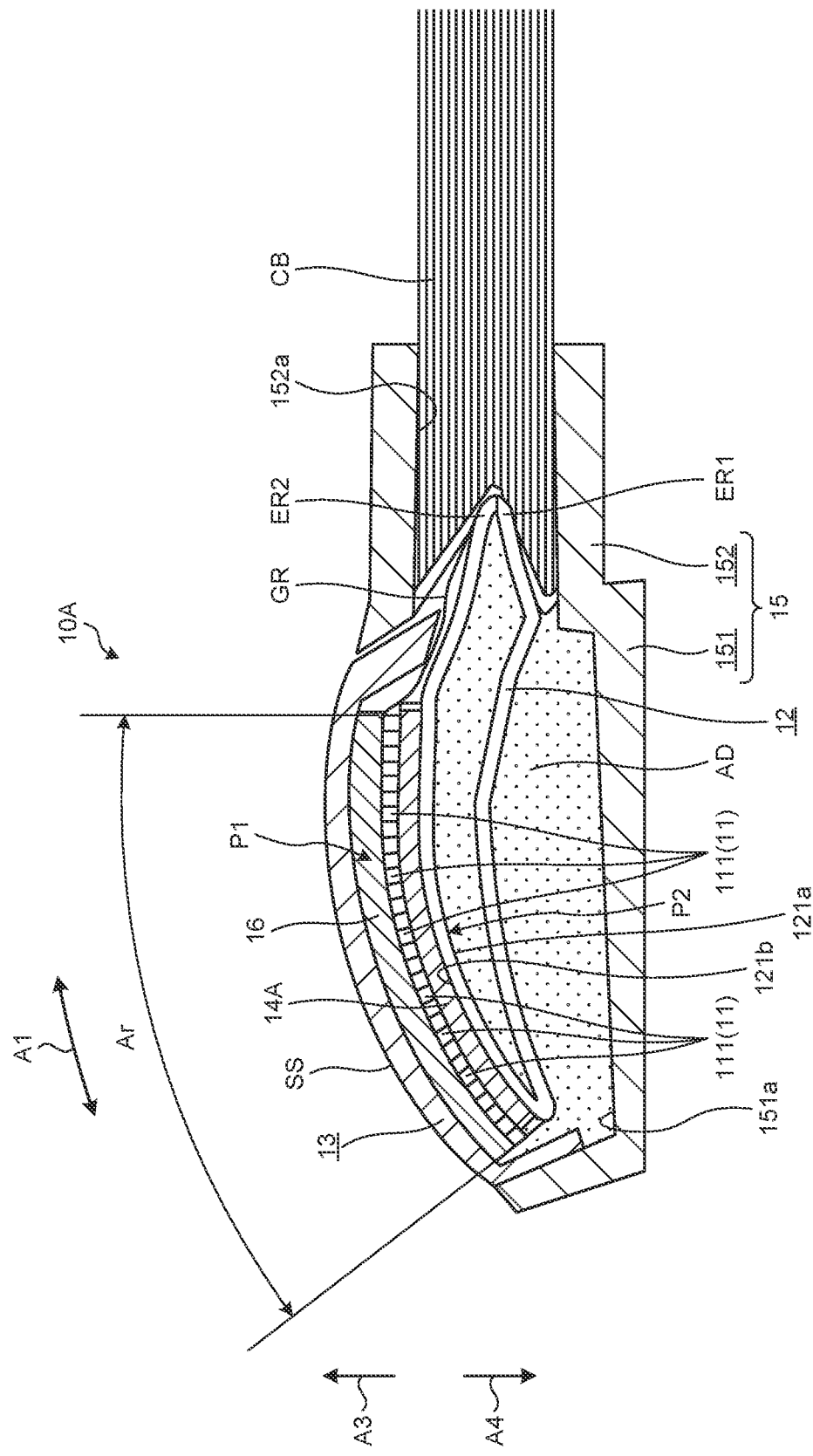
FIG. 7 is a sectional view illustrating an ultrasound probe according to a second embodiment.
Figure 8:
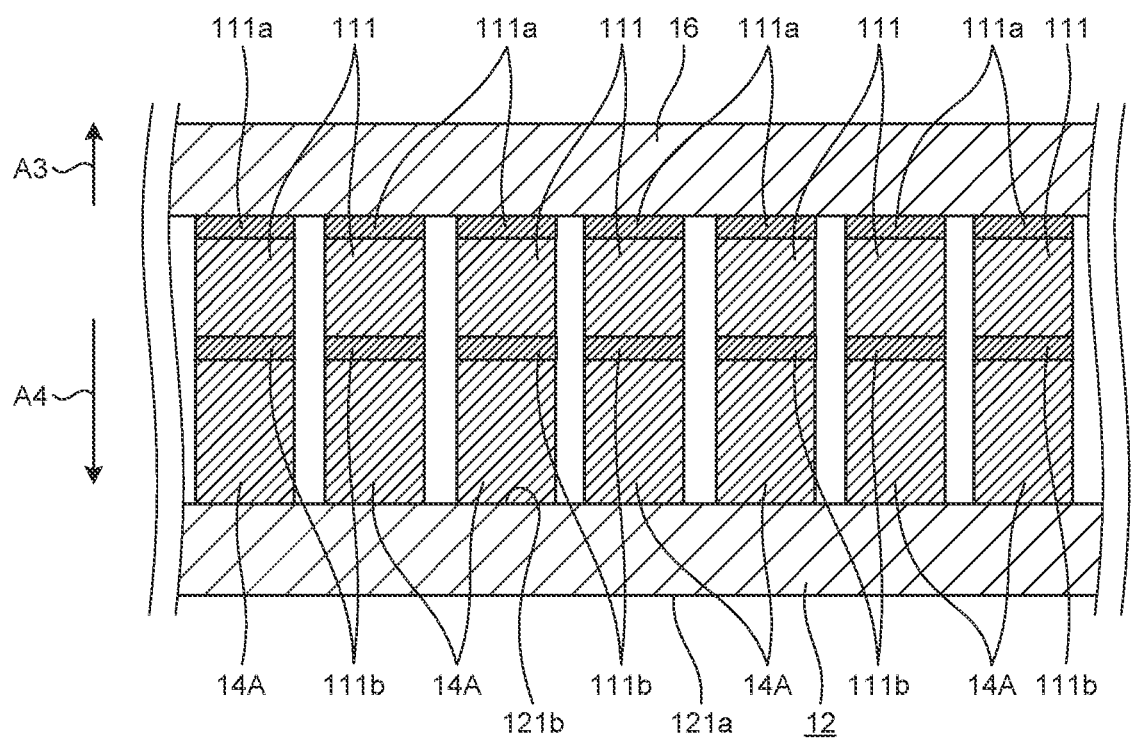
FIG. 8 is an enlarged sectional view of a part of FIG. 7.

FIG. 7 is a sectional view illustrating an ultrasound probe 10A according to the second embodiment. Specifically, FIG. 7 is a sectional view corresponding to FIG. 3. In FIG. 7, for the convenience of explanation, illustration of the electrically conducting layer 122 and insulating layer 123 has been omitted. FIG. 8 is an enlarged sectional view of a part of FIG. 7.

The ultrasound probe 10A according to the second embodiment includes, as illustrated in FIG. 8, a back layer 14A having a form different from that of the back layer 14 in the ultrasound probe 10 described above with respect to the first embodiment. Furthermore, as illustrated in FIG. 7, a part of the wiring member 12 in the ultrasound probe 10A is arranged at the back A4 of the back layer 14A, that is, at a second position P2 that faces the ultrasound transducer 11 with the back layer 14A interposed between the second position P2 and the ultrasound transducer 11, without being arranged at the first position P1 as described above with respect to the first embodiment. Furthermore, an acoustic matching layer 16 is arranged at the first position P1 in the ultrasound probe 10A.

Specifically, as illustrated in FIG. 8, the back layer 14A is provided, for each of the plural piezoelectric elements 111, at the back of the ultrasound transducer 11, and functions as a dematching layer, similarly to the back layer 14 described above with respect to the first embodiment.

Contrary to the wiring member 12 described above with respect to the first embodiment, the wiring member 12 according to the second embodiment is folded back such that the second surface 121b forms an outer front surface of the wiring member 12. In other words, the wiring member 12 is folded back such that the first surface 121a is positioned inside. The vias VI are each connected electrically to the back layer 14A. The plural signal wirings 124 in this second embodiment are respectively connected electrically to the second electrodes 111b (the plural piezoelectric elements 111) via the vias VI and the back layer 14A. That is, the second electrodes 111b function as signal electrodes through which signals are input from and output to the piezoelectric elements 111.

The acoustic matching layer 16 is a member that causes the acoustic impedance of the ultrasound transducer 11 and the acoustic impedance of a subject to match each other, in order to transmit sound (ultrasound) efficiently between the ultrasound transducer 11 and the subject. The acoustic matching layer 16 in this second embodiment is formed of resin having electric conductivity. That is, the acoustic matching layer 16 is electrically connected to each of the first electrodes 111a provided on the plural piezoelectric elements 111. As illustrated in FIG. 7, the ground line GR of the transducer cable CB is electrically connected to the acoustic matching layer 16. That is, the first electrodes 111a function as ground electrodes.

Effects similar to those of the first embodiment described above are also achieved when the ultrasound probe 10A according to the second embodiment described above is adopted.

Other Embodiments

Modes for carrying out the disclosure have been described above, but the disclosure is not to be limited only to the above described first and second embodiments.

The ultrasound probe 10 or 10A in the above described first and second embodiments is a convex ultrasound probe, but without being limited thereto, the ultrasound probe 10 or 10A may be a radial ultrasound probe.

The endoscope system 1 according to the above described first and second embodiments has both the function of generating ultrasound images and the function of generating endoscopic images, but without being limited thereto, the endoscope system 1 may be configured to have just the function of generating ultrasound images.

The endoscope system 1 according to the above described first and second embodiments may be an endoscope system for observation of the interior of a subject, such as a mechanical structure in the industrial field, without being limited to its use in the medical field.

The ultrasound endoscope 2 according to the above described first and second embodiments is an oblique viewing endoscope for observation in a direction intersecting the insertion axis Ax at an acute angle, but the ultrasound endoscope 2 is not limited to this type of endoscope. For example, the ultrasound endoscope 2 may be a side viewing endoscope for observation in a direction intersecting the insertion axis Ax at a right angle, or a direct viewing endoscope for observation in a direction along the insertion axis Ax.

The first and second electrodes 111a and 111b on the piezoelectric elements 111 in the above described first and second embodiments are not necessarily provided at the positions described above with respect to the first and second embodiments, and may be provided at other positions. For example, the first electrodes 111a may be provided on other outer surfaces of the piezoelectric elements 111, in addition to their outer surfaces at the outer front A3, and may be L-shaped in their sectional views. Similarly, the second electrodes 111b may be provided on other outer surfaces of the piezoelectric elements 111, in addition to their outer surfaces at the back A4, and may be L-shaped in their sectional views. Furthermore, the first and second electrodes 111a and 111b may be respectively provided at positions on outer surfaces of the piezoelectric elements 111, with the piezoelectric elements 111 interposed between the first electrodes 111a and the second electrodes 111b, their positions facing each other along the first direction A1.

A layer having electric conductivity may be provided further on the outermost surface, that is, the first surface 121a, of the wiring member 12 in the above described first embodiment, for electrical safety and preventing noise from being mixed into the first and second signal wirings 124a and 124b.

Figure 9:
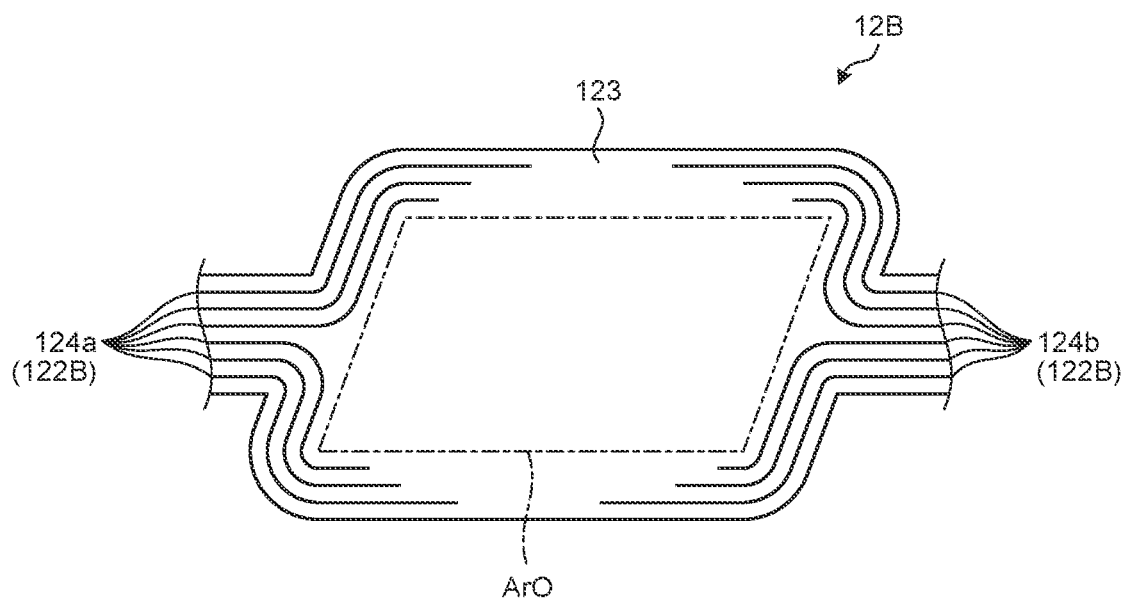
FIG. 9 is a diagram illustrating a first modified example of the first embodiment.

FIG. 9 is a diagram illustrating a first modified example of the first embodiment. Specifically, FIG. 9 is a perspective view of a part (a part arranged at the first position P1) of a wiring member 12B according to the first modified example, as viewed from the outer front A3. In FIG. 9, for convenience of explanation, illustration of the resin layer 121 has been omitted.

An electrically conducting layer 122B different from the electrically conducting layer 122 is adopted for the wiring member 12B according to the first modified example, in contrast to the wiring member 12 described above with respect to the first embodiment.

The electrically conducting layer 122B does not include the plural dummy wirings 125, contrary to the electrically conducting layer 122. Furthermore, the plural first signal wirings 124a and the plural second signal wirings 124b are, as illustrated in FIG. 9, each provided in an area not overlapping an area ArO positioned in the center of the ultrasound transducer 11 when viewed from the outer front A3.

When the wiring member 12B according to the first modified example is adopted, degradation of the acoustic performance due to the electrically conducting layer 122B is able to be prevented because the electrically conducting layer 122B is not provided in the area ArO when viewed from the outer front A3.

Figure 10:
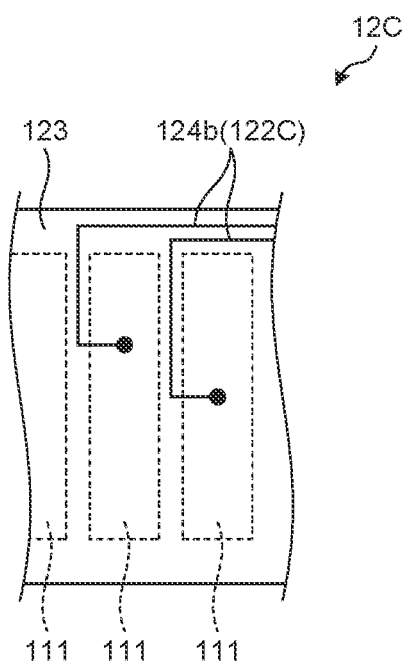
FIG. 10 is a diagram illustrating a second modified example of the first embodiment.

FIG. 10 is a diagram illustrating a second modified example of the first embodiment. Specifically, FIG. 10 is a plan view of a part (a part arranged at the first position P1) of a wiring member 12C according to the second modified example, as viewed from the outer front A3. In FIG. 10, for the convenience of explanation, illustration of the resin layer 121 and plural first signal wirings 124a has been omitted.

An electrically conducting layer 122C different from the electrically conducting layer 122 is adopted for the wiring member 12C according to the second modified example, in contrast to the wiring member 12 described above with respect to the first embodiment.

The electrically conducting layer 122C does not include the plural dummy wirings 125, contrary to the electrically conducting layer 122. Furthermore, parts of the plural second signal wirings 124b are, as illustrated in FIG. 10, provided between adjacent ones of the piezoelectric elements 111 such that the parts do not overlap the plural piezoelectric elements 111 as best they can when viewed from the outer front A3. The plural first signal wirings 124a are provided similarly to the plural second signal wirings 124b.

Effects similar to those of the above described first modified example are also achieved when the wiring member 12C according to the second modified example is adopted.

Figure 11:
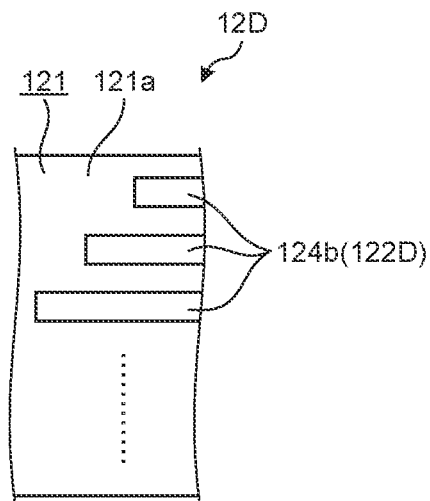
FIG. 11 is a diagram illustrating a third modified example of the first or second embodiment.
Figure 12:
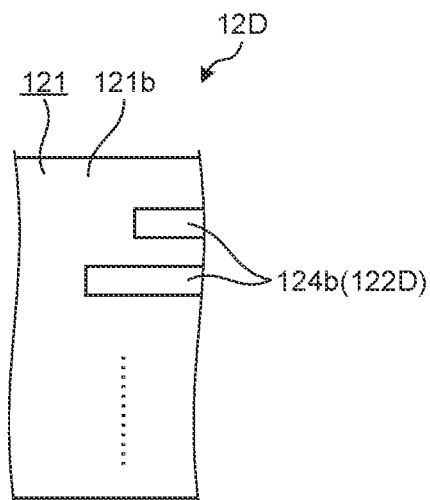
FIG. 12 is a diagram illustrating the third modified example of the first or second embodiment.

FIG. 11 and FIG. 12 are diagrams illustrating a third modified example of the first or second embodiment. Specifically, FIG. 11 is a plan view of a wiring member 12D according to the third modified example, as viewed from the first surface 121a. FIG. 12 is a plan view of the wiring member 12D as viewed from the second surface 121b. In FIG. 11 and FIG. 12, for convenience of explanation, illustration of the plural first signal wirings 124a has been omitted. Furthermore, illustration of the insulating layer 123 has been omitted in FIG. 12.

The electrically conducting layer 122 according to the above described first or second embodiment is provided only on the second surface 121b. That is, the electrically conducting layer 122 is formed of a single layer.

In contrast, an electrically conducting layer 122D provided in the wiring member 12D according to the third modified example is formed of two layers. Specifically, the plural second signal wirings 124b are, as illustrated in FIG. 11, formed of two layers including one layer provided on the first surface 121a and another layer formed on the second surface 121b. The plural first signal wirings 124a are formed similarly to the plural second signal wirings 124b.

When this configuration according to the third modified example is adopted, the distance between adjacent ones of the second signal wirings 124b or between adjacent ones of the first signal wirings 124a becomes longer. Therefore, mutual interference between signals through adjacent ones of the second signal wirings 124b or through adjacent ones of the first signal wirings 124a is reduced. In other words, cross talk is reduced.

Figure 13:
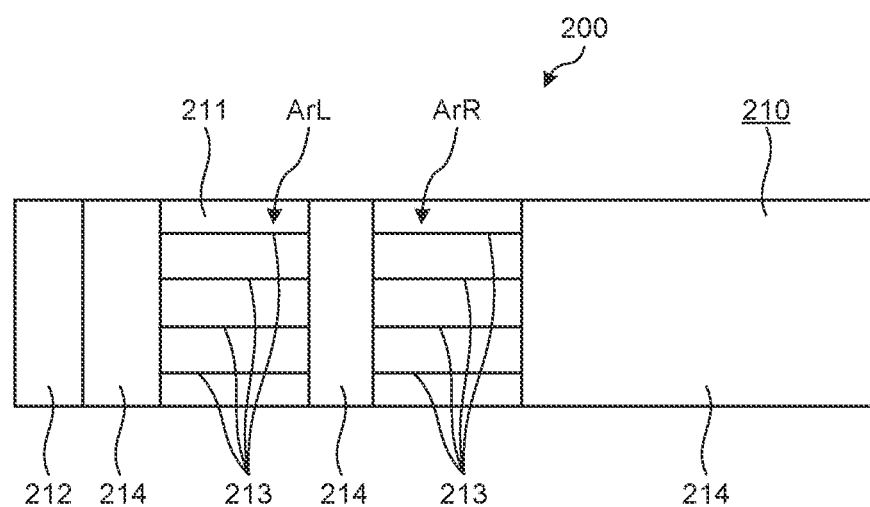
FIG. 13 is a diagram illustrating a fourth modified example of the first or second embodiment.
Figure 14:
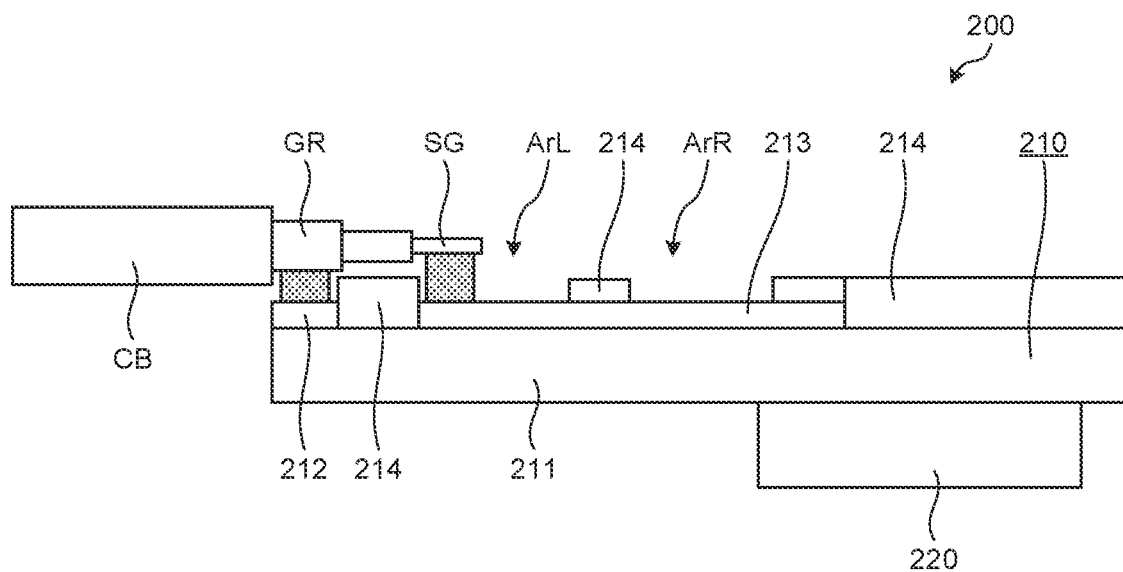
FIG. 14 is a diagram illustrating the fourth modified example of the first or second embodiment.

FIG. 13 and FIG. 14 are diagrams illustrating a fourth modified example of the first or second embodiment. Specifically, FIG. 13 and FIG. 14 are diagrams illustrating a configuration of a connecting member 200 that is provided in the endoscope connector 9 and electrically connects the transducer cable CB and the ultrasound cable 31 to each other. FIG. 13 is a plan view of an FPC 210. FIG. 14 is a side view of the connecting member 200.

The connecting member 200 illustrated in FIG. 13 and FIG. 14 may be adopted in the endoscope system 1 according to the first or second embodiment described above.

The connecting member 200 includes, as illustrated in FIG. 13 or FIG. 14, the FPC 210 and a connector 220 (FIG. 14).

The FPC 210 includes, as illustrated in FIG. 13 or FIG. 14, a circuit board 211, a ground pad 212, plural (four in this third modified example) signal pads 213, and a cover member 214.

The circuit board 211 is a circuit board that includes a ground line (not illustrated in the drawings) and plural signal lines (not illustrated in the drawings) provided in an elongated board formed of an insulating material, such as polyimide.

The ground pad 212 is provided at an end portion on the circuit board 211, the end portion being in the direction of the transducer cable CB (on the left in FIG. 13 and FIG. 14) and has electrical continuity to the ground line (not illustrated in the drawings) inside the circuit board 211. The ground line GR of the transducer cable CB is electrically connected to the ground pad 212, as illustrated in FIG. 14.

The plural signal pads 213 are provided on the right, in FIG. 13 and FIG. 14, of the ground pad 212, on the circuit board 211. These plural signal pads 213 each extend along a longitudinal direction of the circuit board 211, that is, in a left-right direction in FIG. 13 and FIG. 14, and are arranged in parallel along a width direction of the circuit board 211, that is, in an up-down direction in FIG. 13). End portions of the plural signal pads 213 have electrical continuity respectively to the plural signal lines (not illustrated in the drawings) inside the circuit board 211, the end portions being on the right in FIG. 13 and FIG. 14.

The cover member 214 is formed of an insulating material, such as coverlay. The cover member 214 is provided across the plural signal pads 213 and partitions the plural signal pads 213 into a left area ArL and a right area ArR in FIG. 13 and FIG. 14.

Plural signal lines SG of the transducer cable CB are respectively connected electrically to the plural signal pads 213 in the area ArL, as illustrated in FIG. 14. The plural signal pads 213 in the area ArR, on the other hand, function as pads for testing electric pathways leading to the plural signal lines SG from the plural piezoelectric elements 111.

In the example of FIG. 13 and FIG. 14, the cover member 214 is also provided, on the circuit board 211, between the ground pad 212 and the plural signal pads 213, and on the end portion on a right side of the plural signal pads 213 in FIG. 13 and FIG. 14.

The connector 220 is a connector that electrically connects between: the ground line (not illustrated in the drawings) and plural signal lines (not illustrated in the drawings) that are both inside the circuit board 211; and the ultrasound cable 31.

An ultrasound probe according to the disclosure is able to be downsized without being degraded in acoustic performance.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound probe, comprising:
   an ultrasound transducer including plural piezoelectric elements, each piezoelectric element configured to emit ultrasound according to an electric signal input;
   an acoustic lens layer configured to radiate the ultrasound emitted from the plural piezoelectric elements to outside;
   an electrically conductive back layer facing the acoustic lens layer with the ultrasound transducer interposed between the back layer and the acoustic lens layer; and
   a wiring member arranged at a first position between the acoustic lens layer and the ultrasound transducer, the wiring member is further arranged at a second position facing the ultrasound transducer with the back layer interposed between the second position and the ultrasound transducer;
   wherein the wiring member includes:
      an electrically insulating resin layer; and
      an electrically conducting layer provided on the resin layer and including plural signal wirings through which the electric signals that respectively cause the plural piezoelectric elements to emit the ultrasound are supplied to the plural piezoelectric elements, the plural signal wirings being respectively connected electrically to the plural piezoelectric elements.

2. The ultrasound probe according to claim 1, wherein the plural signal wirings have different lengths in a longitudinal direction of the resin layer.

3. The ultrasound probe according to claim 1, wherein the wiring member further includes an insulating layer facing the resin layer with the electrically conducting layer interposed between the insulating layer and the resin layer, and
   the plural signal wirings are respectively connected electrically to the plural piezoelectric elements via plural vias provided in the insulating layer.

4. The ultrasound probe according to claim 1, wherein the electrically conducting layer includes dummy wirings made of a same material as a material of the signal wirings, the dummy wirings having a same thickness as a thickness of the signal wirings.

5. The ultrasound probe according to claim 1, wherein the plural signal wirings include:
   a first signal wiring extending, on the resin layer, from a first end toward a second end of the resin layer, the first end and the second end being at ends of a longitudinal length of the resin layer, and
   a second signal wiring extending from the second end to the first end, on the resin layer.

6. The ultrasound probe according to claim 1, wherein the back layer is electrically connected to the ultrasound transducer.

7. The ultrasound probe according to claim 6, wherein at least a part of the wiring member is arranged at the first position and has an acoustic impedance between an acoustic impedance of the plural piezoelectric elements and an acoustic impedance of the acoustic lens layer.

8. The ultrasound probe according to claim 7, wherein
   the back layer includes a dematching layer electrically connected to the plural piezoelectric elements and having an acoustic impedance larger than the acoustic impedance of the plural piezoelectric elements, and
   a ground line serving as a ground is electrically connected to the back layer.

9. The ultrasound probe according to claim 6, wherein
   the back layer includes plural dematching layers respectively provided for the plural piezoelectric elements, the plural dematching layers having an acoustic impedance larger than an acoustic impedance of the plural piezoelectric elements,
   at least a part of the wiring member is further arranged at a second position facing the ultrasound transducer with the back layer interposed between the second position and the ultrasound transducer, and
   the plural signal wirings are respectively connected electrically to the plural piezoelectric elements via the plural dematching layers.

10. An ultrasound endoscope comprising:
    an insertion portion configured to be inserted into a subject, the insertion portion including, at a distal end of the insertion portion:
       an ultrasound transducer including plural piezoelectric elements, each piezoelectric element configured to emit ultrasound according to an electric signal input;
       an acoustic lens layer configured to radiate the ultrasound emitted from the plural piezoelectric elements to outside;
       an electrically conductive back layer facing the acoustic lens layer with the ultrasound transducer interposed between the back layer and the acoustic lens layer; and
       a wiring member arranged at a first position between the acoustic lens layer and the ultrasound transducer, the wiring member is further arranged at a second position facing the ultrasound transducer with the back layer interposed between the second position and the ultrasound transducer;
    wherein the wiring member includes:
       an electrically insulating resin layer; and
       an electrically conducting layer provided on the resin layer and including plural signal wirings through which the electric signals that respectively cause the plural piezoelectric elements to emit the ultrasound are supplied to the plural piezoelectric elements, the plural signal wirings being respectively connected electrically to the plural piezoelectric elements.

11. The ultrasound probe according to claim 10, wherein
    the wiring member further includes an insulating layer facing the resin layer with the electrically conducting layer interposed between the insulating layer and the resin layer, and
    the plural signal wirings are respectively connected electrically to the plural piezoelectric elements via plural vias provided in the insulating layer.

12. The ultrasound probe according to claim 10, wherein the plural signal wirings include:
  a first signal wiring extending, on the resin layer, from a first end toward a second end of the resin layer, the first end and the second end being at ends of a longitudinal length of the resin layer, and
  a second signal wiring extending from the second end to the first end, on the resin layer.

13. The ultrasound probe according to claim 10, wherein at least a part of the wiring member is arranged at the first position and has an acoustic impedance that is between an acoustic impedance of the plural piezoelectric elements and an acoustic impedance of the acoustic lens layer.

14. The ultrasound probe according to claim 13, wherein
  the back layer includes a dematching layer electrically connected to the plural piezoelectric elements and having an acoustic impedance larger than the acoustic impedance of the plural piezoelectric elements, and
  a ground line serving as a ground is electrically connected to the back layer.

15. The ultrasound probe according to claim 10, wherein
  the back layer is electrically connected to the ultrasound transducer,
  the back layer includes plural dematching layers respectively provided for the plural piezoelectric elements, the plural dematching layers having an acoustic impedance larger than an acoustic impedance of the plural piezoelectric elements,
  at least a part of the wiring member is arranged at the second position, and
  the plural signal wirings are respectively connected electrically to the plural piezoelectric elements via the plural dematching layers.

* * * * *